United States Patent [19]

Merril et al.

[11] Patent Number: 4,508,820
[45] Date of Patent: Apr. 2, 1985

[54] METHOD FOR SIMULTANEOUSLY MONITORING TURNOVER RATE IN MULTIPLE PROTEINS

[75] Inventors: Carl R. Merril, Rockville; David Goldman, Gaithersburg, both of Md.

[73] Assignee: The United States of America as represented by the Department of Health and Human Services, Washington, D.C.

[21] Appl. No.: 582,862

[22] Filed: Feb. 27, 1984

Related U.S. Application Data

[63] Continuation of Ser. No. 407,762, Aug. 13, 1982, abandoned.

[51] Int. Cl.³ .......................... C12Q 1/29; C12Q 1/16; G01T 1/00
[52] U.S. Cl. ...................................... 435/29; 424/1.1; 435/35
[58] Field of Search .................... 436/504; 425/29, 35; 424/1.1

[56] References Cited

PUBLICATIONS

Switzer III, et al., Analytical Biochem., 98, (1), 231–237, (1979).
Merril et al., Analytical Biochem., 110, (1), 201–207, (1981).
Merril et al., Proc. Natl. Acad. Sci., U.S.A., 76, (9), 4335–4339, (1979).
Merril et al., Science, 211, (4489), 1437–8, (1981).
Van Keuren et al., Analyt. Biochem., vol. 116, (1981), 248–255.
Mafart et al., Chem. Abstracts, vol. 94, (1981), #135432d.
Kucukalic et al., Chem. Abstracts, vol. 89, (1978), #176958v.
Milenkovic, Chem. Abstracts, vol. 90, (1979), #85652v.
"Variations in Expression of Mutant β Actin Accompanying Incremental Increases in Human Fibroblast Tumorigenicity", *Cell*, 28: 259–268, (1982).

*Primary Examiner*—Christine M. Nucker
*Attorney, Agent, or Firm*—Holman & Stern

[57] ABSTRACT

The invention provides an assay method for cellular and extracellular protein biodynamics comprising the use of radiochemical techniques in combination with high resolution protein separation procedures and recently developed silver stain techniques, to assess turnover of polypeptides over time. Quenching of polypeptide radiolables in silver stained gels is obviated by the use of $^{14}$C-labelled amino acids as precursors.

4 Claims, 3 Drawing Figures

METHOD FOR SIMULTANEOUSLY MONITORING TURNOVER RATE IN MULTIPLE PROTEINS

GOVERNMENT SPONSORSHIP

Development of this invention was supported by the National Institute for Alcohol Abuse and Alcoholism and the National Institute of Mental Health.

This is a continuation of application Ser. No. 06/407,762, filed Aug. 13, 1982, now abandoned.

BACKGROUND OF THE INVENTION

The metabolism of proteins by microorganisms or other cellular entities is of particular interest in view of the known relationship of protein "turnover" rate and various physiological states. Since the synthesis and degradation of cellular and extracellular proteins are normally carefully regulated by the body, variations in the combined synthesis and degradation rates, termed "turnover" rate, may be diagnostic of normal or abnormal physiologic events. For example, changes in the turnover rate of heart mitochondrial or microsomal proteins may signify incipient disease, or induction or reduction of globins or enzymes which may be a response to unusual levels of regulating factors such as steroid hormones. Thus, methods for assessing synthesis and degradation rates of proteins are particularly desirable, both from the standpoint of identifying normal or abnormal inducing events and of relating turnover rate to specific disease states in diagnostic applications.

Radioactive labelling procedures are widely used as a means of measuring the metabolic activity of microorganisms. Specifically, the synthesis of various cellular constituents can be assessed by quantification of rates and amounts of incorporation of radioactive materials into the cellular constituents of microorganisms. Known radiochemical techniques are, however, insufficient by themselves to simultaneously quantify multiple protein turnover rates, as these techniques are generally inherently limited to a determination of the rater of either synthesis or degradation of a given molecule. For example, in an equilibrium labelling format, a steady state microorganism culture may be presented with a radioactivity labelled metabolite, and samples removed at stated intervals; the test molecule, such as protein, is then isolated and its radioactive content determined. While the resultant data reflects the rate of incorporation of the labelled metabolite into the synthesized test protein molecule, the procedure does not yield data sufficient to simultaneously determine turnover rate of specific proteins. Accordingly, when it is desired to evaluate protein turnover rate, radiolabelling is used in conjunction with procedures for resolving protein mixtures and determining the concentration of proteins of interest.

SUMMARY OF THE INVENTION

The invention provides an assay method for cellular and extracellular protein biodynamics comprising the use of radiochemical techniques in combination with high resolution protein separation procedures and recently developed silver stain techniques, to assess turnover of polypeptides over time. It has unexpectedly been found that the use of $^{14}C$-labelled precursors permits the use of radiolabelling techniques in conjunction with silver staining methods for polypeptides in gels, and by the simple, yet highly sensitive, process of the invention, net synthesis or degradation in vivo or in vitro of specific proteins under varying experimental conditions may be quantified. Exemplary conditions are those promoting homeostasis, or those conditions which stimulate or reduce protein synthesis.

The process of the invention is particularly useful in both research and diagnostic applications for quantifying multiple protein turnover rates. Potential applications include evaluation of trauma or in monitoring genetically altered microbes. For example, central nervous system damage might be evaluated by a determination of the rate of exchange of albumin between blood and spinal fluid. In this determination, radio-labelled ($^{125}I$) iodine would be injected intravenously, and the specific activity ($^{125}I$-albumin/total albumin) in the spinal fluid measured. Alternatively, in genetic engineering applications, microbial production of critical enzymes can be monitored by the present process, for example by measuring specific activities (by pulse labelling) under different growth conditions. Production of specific cell enzymes can thus be maximized.

The process of the present application further is useful in a number of research applications, for example, in mutagenesis assays. Alterations in cellular protein synthesis owing to mutation of controlling genes can be assessed by combining silver staining methods and high resolution protein separation techniques, in conjunction with radioactive labelling, as described herein. An exemplary application is the $\beta$-actin turnover rate analysis described by Leavitt, et al., in Cell, 28, 259–268 (1982), therein determined by standard gel electrophoresis separation combined with pulse-chase labelling.

DETAILED DESCRIPTION OF THE INVENTION

Figure 1A:
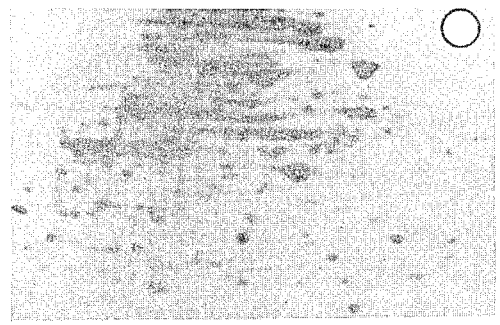
FIG. 1: Fluorograms of $^3H$-containing gels.
  (a) Unstained gels
  (b) Histological silver stained gels
  (c) Photographic silver stained gels
  (d) Histological silver stain followed by removal of silver
  (e) Photographic silver stain followed by removal of silver

According to the process of the present invention, known silver staining techniques for quantifying total protein content of sample fluids are employed in conjunction with known radioactive labelling techniques for quantifying the rate of protein synthesis or degradation in the same sample fluids to obtain a protein turnover rate quantitatively reflective of protein metabolism. The protein turnover rate can be expressed as $(-)dc/dt$, wherein dc is the increase (or decrease) in specific activity of total protein and dt is the time elapsed. For a first-order reaction, wherein the rate of reaction is directly proportional to the concentration, the reaction rate may be calculated by solving for the velocity constant k in the following elementary equation:

$$k = \frac{2.303}{\Delta t} \log \frac{C_o}{C}$$

wherein $C_o$ is the specific activity of a sample ($C_{RP}/C_{TP}$) at the beginning of the reaction when the time is zero, and C is the specific activity of the sample after time t has elapsed. The effective half-life of the protein may be calculated from k according to known principles, as follows:

$$t_{\frac{1}{2}} = 0.693/k$$

By the process of the present invention, the specific activity of a given protein sample is calculated as the radioactivity of the specific protein versus the total specific protein present in the sample at a given time. For a steady state radioactively labelled sample introduced into a media containing only unlabelled amino acids, the radioactivity of a given sample ($C_{RP}$) proportionally reflects the amount of undegraded original protein, while the measurement of total protein ($C_{TP}$) reflects the amount of undegraded original protein plus synthesized protein present in the sample. From data obtained for $C_{RP}$ and $C_{TP}$, specific activities of each sample ($C_{RP}/C_{TP}$), relating protein degradation to protein synthesis are calculated at given intervals. The particular protein metabolic rate is then determined as the net change in specific activity of the protein sample over time according to the equations set forth supra. Conversely, a steady state unlabelled sample may be employed, and introduced into media containing only radioactively labelled amino acids; in this instance, the radioactivity of a given sample will closely approximate the amount of newly synthesized protein, while the measurement of total protein will reflect the amount of undegraded original protein plus newly synthesized protein. The specific activities for each sample are then similarly calculated.

The silver staining methods employed to obtain a measurement of total protein content of a given biological sample comprise the photographic silver stain techniques described in the copending U.S. patent application of Carl R. Merril, Ser. No. 240,577, filed Mar. 4, 1981, and the references cited therein, particularly the techniques described in Karcher, Lowenthal and Van Soom, in "Cerebrospinal Fluid Proteins Electrophoresis Without Prior Concentration", *Acta neurol. Belg.*, 79, 335–337 (1979), Switzer, Merril and Shifrin in "A Highly Sensitive Silver Stain For Detecting Proteins And Peptides In Polyacrylamide Gels", *Anal. Biochem.*, 98, 231–237 (1979), Merril, Switzer and Van Keuren in "Trace Polypeptides In Cellular Extracts And Human Body Fluids Detected By Two-Dimensional Electrophoresis And A Highly Sensitive Silver Stain", *Proc. Natl. Acad. Sci. U.S.A.*, 76, 4335–4339 (1979), and Oakley, Kirsch and Morris in "A Simplified Ultrasensitive Silver Stain For Detecting Proteins In Polyacrylamide Gels", *Anal. Biochem.*, 105, 361–363 (1980). The Merril application, Ser. No. 240,577 and the references cited therein are incorporated by reference herein. Additionally, known histological silver stains of the type described in the Merril application, supra, are employable, although less satisfactory results are frequently obtained. The photographic silver stains are particularly used, in accordance with the prior art, in gel electrophoresis or comparable analytical processes. Typically, the polypeptide is fixed in a suitable gel, such as a polyacrylamide gel, and treated with an oxidizing agent to effect photoreversal; a latent image is then formed by exposure to a photosensitive salt solution and actuating radiation. The latent image is then developed and the resultant electrophoretic patterns examined for particular polypeptides and concentrations as related to stain densities.

Protocols for radiochemical procedures useful in the process of the present invention are well known, broadly comprising incubating a culture in the presence of radioactively labelled metabolite or precursors thereof. Labelling formats typically employed comprise pulse labelling, equilibrium labelling, and pulse-chase labelling, and are experimentally designed to monitor the synthesis or degradation of a given molecule. In all of these formats, the presence of radioactive material in the cellular constituents of the cultured microorganism is measured at stated intervals to determine the rate of metabolism of the substrate material under the designated experimental conditions. Typically, the radioactive content is measured by techniques such as autoradiography or scintillation counting.

According to the broad process of the present invention, cell cultures are first incubated with a radioactive substrate marker detectable by usual radioactive measurement techniques. At intervals, cell samples are isolated from the culture medium, lysed, and proteins extracted. The extracted proteins are then subjected to gel electrophoresis, silver stained, and the total specific protein content of each spot measured. The gel is then dried, and the radioactivity of each spot measured. Customarily, the densities of the silver stains are obtained by sensitive microdensitometric measurements and are compared to standards to obtain a value for total protein content expressed in milligrams or micrograms. The radioactivity of each spot is conveniently measured by scintillation counting in counts per minute, which is proportional to the amount of radioactive protein present in each spot. Alternatively, the radioactive content of each spot is measured by autoradiography or fluorography. Standards of known specific radioactivity are employed to calibrate the autoradiograms or fluorograms.

The cell cultures employed may be of any biological derivation, such as cells present in cerebrospinal and amniotic fluids, blood, or various organs such as heart microsomal or mitochondrial cells.

The radioactive labels useful in the process of the present invention comprise $^{14}C$-labelled amino acids. It has been unexpectedly found that the radioactive content of proteins labelled with $^{14}C$ isotope is measurable by autoradiography, fluorography, or scintillation counting after silver staining according to the process of the present invention, whereas tritium ($^3H$-labelled) amino acids are quenched by the silver staining techniques employed to the extent that $^3H$-labelled proteins are substantially undetectable by fluorography, autoradiography, or scintillation counting.

Autoradiograms of gels containing $^{14}C$-labelled proteins which have been silver stained can be quantified by measurement of the protein spot densities, as any minor quenching effect alters all densities by substantially the same ratio. The use of autoradiograms in conjunction with the photographic silver stain method is preferred, as less quenching occurs with photographic silver stain than with histologic silver stain. Further, any quenching of $^{14}C$ can, in both instances, be substantially overcome by merely extending the exposure time of the gel to the X-ray film. Fluorographic measurement of radioactivity is useful in conjunction with photochemical silver stained $^{14}C$-labelled proteins, as the quenched fluorographic image is restorable by removal of the photochemical silver from the gel by photographic reducer as described by Switzer, et al., *Anal. Biochem.*, 98, supra. This procedure, however, does not restore the fluorographic image with histologically silver stained proteins. Scintillation counting effectively reflects the radioactive content of $^{14}C$-labelled proteins stained with either photographic or histologic silver stain.

In an exemplary embodiment of the present invention, cells are preincubated in the presence of a nutrient medium containing a mixture of $^{14}C$-labelled amino acids for several generations until an equilibrium state is reached. The cells are then removed to a nutrient medium containing only unlabelled amino acids, and cultured over a period of time. At intervals of, for example, ½ to 2 hours, a sample of the culture is removed from the culture medium, and the cells are lysed and the cellular proteins extracted. If bacteria are being studied, the intervals are in minutes while for animal and plant cells, the intervals are measured in hours. The sample proteins are electrophoresed, and then silver stained, and the total protein content of each of the spots of the sample calculated. The gel is then dried and the spots subjected to autoradiography or scintillation counting to determine the amount of radioactive protein present in each spot of the sample. For each sample, the specific activity of each spot is calculated as, for example, CPM per milligram of total protein. The velocity constant k is then calculated for the time elapsed, and the effective half-life of the protein established according to the equation:

$$t_{\frac{1}{2}} = 0.693/k.$$

In this embodiment, the radioactive protein content of the samples is expected to decrease over time, reflecting continuous degradation of the radioactively labelled proteins in the original steady state culture. For a protein with a constant turnover rate, the total protein however will remain constant during the course of the experiment. If turnover rate is not constant, for example, if an inducer is added to the culture, total protein will be expected to vary over the course of the experiment to reflect this event. The data obtained for $C_{RP}$ and $C_{TP}$ for each sample spot may be plotted as a function of time, desirably on the same graph.

In an alternate embodiment, $^{14}C$-labelled amino acids are introduced into a steady state culture preincubated in the presence of unlabelled amino acids. At similar intervals, a sample of the culture is removed from the nutrient medium, the cells are lysed, and the extracted protein electrophoresced by, for example, two-dimensional gel electrophoresis. The gel is then silver stained, and the total protein content of each of the resultant spots of the sample calculated. After drying the gel, the amount of radioactivity of each spot is measured to determine the radioactive protein content of each spot. The specific activity of each spot is then calculated for each sample as previously described.

In this embodiment, the radioactive protein content of the samples is expected to increase over time, reflecting continuous synthesis of proteins from labelled amino acids. For a protein with a constant turnover rate, the total protein content will again remain constant during the course of the experiment, since the rate of degradation of original protein will equal the rate of synthesis of radioactive protein. If turnover rate is not constant, total protein values will fluctuate over time as the rate of synthesis exceeds or falls below the rate of degradation.

While the equilibrium labelling formats described in these embodiments are generally useful, a pulse-labelling format is generally employed, which minimizes the possibility that degradation products of the original proteins will be resynthesized, thus inaccurately reflecting either synthesis or degradation rates. Both formats, and other formats, are well known in the art, and are described in detail in many texts.

The autoradiographic and fluorographic techniques useful in the process of the present invention are also well known, typically involving exposure of the active material to X-ray film to obtain photographic negatives of autoradiograms and fluorograms bearing detectable images. Typically, the densities of the spot images obtained on the autoradiograms and fluorograms are proportional to the radioactive protein content of these images. The radioactivity of these spots is conveniently expressed in terms of CPM for use in quantifying the data according to the present invention, by submitting the exposed autoradiograms or fluorograms to a scintillation counter.

The following Examples are included as illustrative of the practice of the invention:

EXAMPLE I

Cell Culture Conditions

Mouse fibroblast cells, A9, were grown in plastic Falcon 75 cm² flasks in 15 ml of Alpha Essential Medial supplemented with 5% fetal calf serum. Cultures were maintained at 37° C. in a 5% $CO_2$ humidified incubator.

Radioisotope Incorporation And Protein Extraction

Separate flasks of 70–90% constituent cells were labelled with 50 μCi of $^{14}C$-amino acid mixture and 150 μCi of $^3H$-amino acid mixture, in media depleted of unlabelled amino acids, for four (4) hours.

At ½ hour intervals, 10 samples of about $10^6$ cells were taken, followed by lysing and extraction of the cytoplasmic proteins with Triton X-100 in the solubilization procedure described by Milman, et al., *Proc. Nat'l. Acad. Sci.*, 73, 4589–4593 (1976). The amount of radioactivity in each sample was determined by precipitating an aliquot with cold 10°/0 trichloroacetic acid (TCA).

Electrophoresis

Two-dimensional electrophoresis was performed according to O'Farrell, *J. Biol. Chem.*, 250, 4007–20021 (1975), using isoelectric focussing 4:1 mixture of Biolytes (Biorad Company) pH range 5/7 and 3/10 in the first dimension and electrophoresis through a uniform gel of 10% acrylamide in the second dimension. Half of the gels (5) were each loaded with $2.5 \times 10^6$ CPM of TCA-precipitable $^3$H counts and the other half with $10^6$ CMP of $^{14}$C.

Staining

Following electrophoresis, one of each of the $^3$H and $^{14}$C-labelled gels were left unstained, but were soaked overnight in a fixative containing 50% methanol and 12% acetic acid. Two sets of gels were each stained with the two silver stains (histologic and photographic). Silver was immediately removed fom one set of gels using photographic reducer, according to the process of Switzer, et al., *Anal. Biochem.*, 98, supra. The gels obtained are described in Table 1.

Autoradiography And Fluorography

All gels were treated for fluorographic enhancement with Enhance. Then after agitation for a few minutes in a solution of 3% glycerol and 7% acetic acid to prevent cracking, they were dried under vacuum and mild heat. The dried gels were exposed to Kodak XR-2 X-ray film in an X-ray film holder containing intensifying screens. For the $^3$H containing gels, the film had been pre-fogged according to Laskey and Mills. EXposure was at $-70°$ C. for four (4) days. Autoradiograms and fluorograms were photographed next to a density standard (to normalize the densities) on a light box with a Mamiya RB Pro camera, using Kodax Tri-X 120 mm film.

Density Measurement

Photographic negatives of autoradiograms and fluorograms bearing detectable spots were scanned on an Optronics P-1000HS scanning densitomer at 100 microns resolution using the "3D" optical density range. The data was processed with a PDP 11/60 computer equipped with a DeAnza IP5000 image processor. The density standard was used to normalize the computer images to correct for variations in photographic and scanning techniques. The densities of thirteen (13) identical protein spots (of non-saturating densities) on each gel were measured. Backgrounds were estimated for each protein by construction of density histograms of gel subregions and identification of the modal densities.

Measurement Of Radioactivity In Gel Spots

After autoradiographic or fluorographic exposure was complete, three (3) identical protein spots were cut out with a scalpel from the $^3$H-containing gels, and five (5) from the $^{14}$C gels. Each excised protein was placed in a scintillation vial, and rehydrated with 50 μl of water for one (1) hour. To each was added 1.0 ml of solubilizer (90% NCS solubilizer and 10% water), and the vials were incubated in a 50° C. oven for two (2) hours. After cooling, 10 ml of scintillation cocktail (Research Products International Corp.) were added to each, and they were counted in a Beckman LS9000 Liquid Scintillation Counter.

Results

Figure 1B:
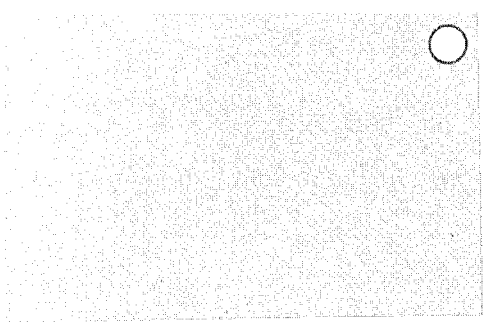
Figure 1C:
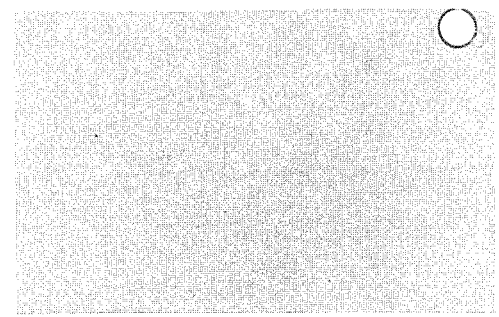
Figure 1D:
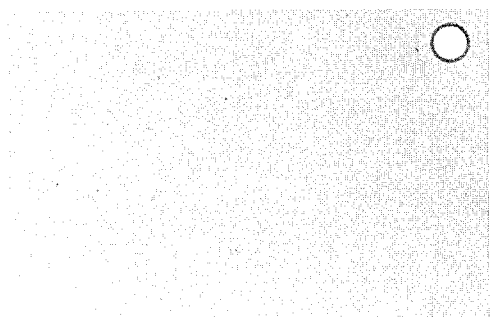
Figure 1E:
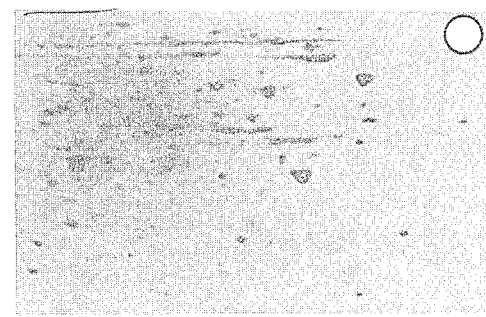
Figure 2A:
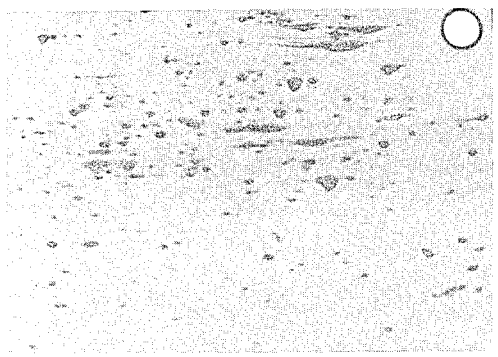
FIG. 2: Autoradiograms of $^{14}C$-containing gels.
  (a) Unstained gels
  (b) Histological silver stained gels
  (c) Photographic silver stained gels
  (d) Histological silver stain followed by removal of silver
  (e) Photographic silver stain followed by removal of silver
Figure 2B:
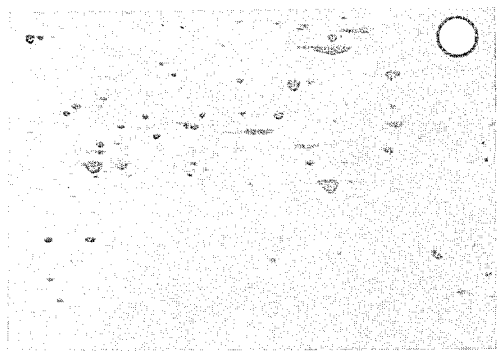
Figure 2C:
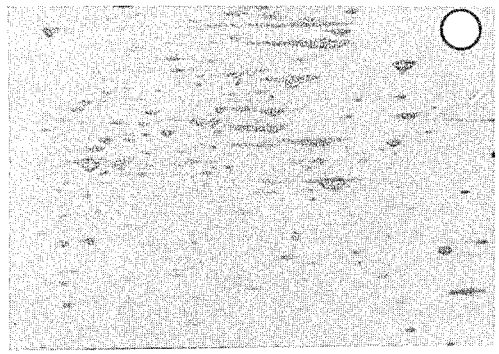
Figure 2D:
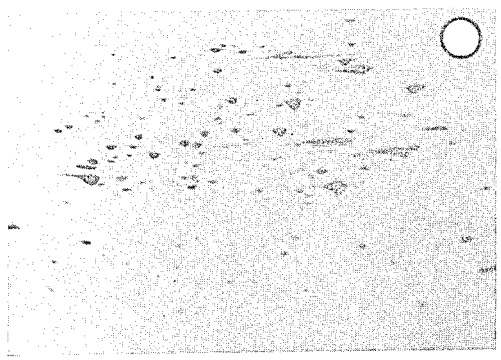
Figure 2E:
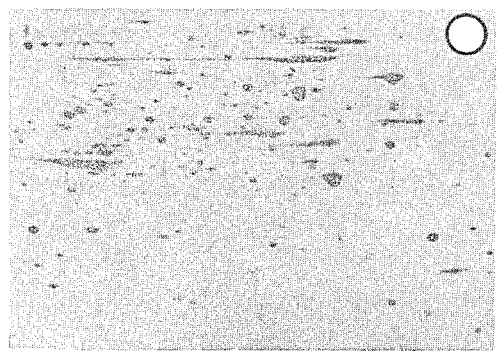

Photographs of the autoradiograms and fluorograms are shown in FIGS. 1 and 2. The histological silver stain completely quenched detection by fluorography of $^3$H-labelled proteins. Even removal of the silver from the gel by photographic reducer did not restore the ability to detect the $^3$H-labelled proteins. The photographic silver stain (which uses less silver nitrate per gel) also quenched $^3$H-labelled proteins. However, several proteins are faintly visible with a few major proteins showing a darker area at their periphery. Removal of the silver restored images of the $^3$H-labelled proteins, but not to the intensity obtained by fluorography of the unstained gel. For the $^{14}$C-labelled proteins, there is a slight diminution in the autoradiographic intensities of the labelled proteins in the silver stained gels and in those with the silver removed. This effect is stronger for the histological stain that the photographic stain, which has little effect.

Table 1 shows the average CPM of the solubilized cut-out proteins from $^3$H and $^{14}$C gels (after subtraction of background CPM), as a percentage of the CPM from the unstained gel. The data is in general agreement with what can be seen on the autoradiograms or fluorograms. The histological silver stain results in more quenching of radioactivity than does the photographic silver stain, and the effect is more severe for $^3$H than for $^{14}$C.

Figure 3A:
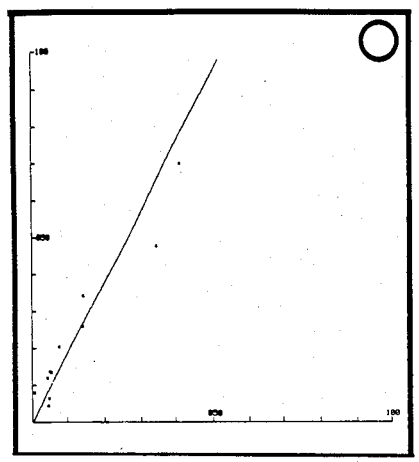
FIG. 3: Density versus density graphs of individual protein densities on autoradiograms and fluorograms as measured with a PDP 11/60 computer equipped with an image processor. Densities of the 20 protein spots in the unstained $^{14}C$ gel (y-axis) are compared with the densities of the corresponding protein spots in stained gel (x-axis).
  (a) The histological silver stained gel is on the x-axis. ($r=0.97$)
  (b) The photographic silver stained gel is on the x-axis. ($r=0.99$)
  (c) The histological silver stained gel (from which the silver was removed) is on the x-axis. ($r=0.92$)
  (d) The photographic silver stained gel (from which the silver was removed) is on the x-axis. ($r=0.82$).
Figure 3B:
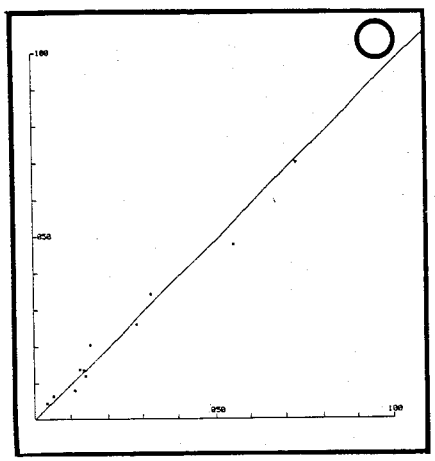
Figure 3C:
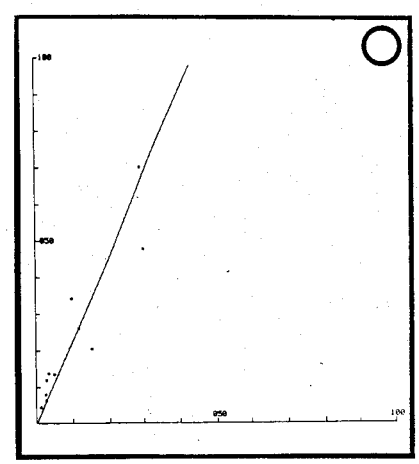
Figure 3D:
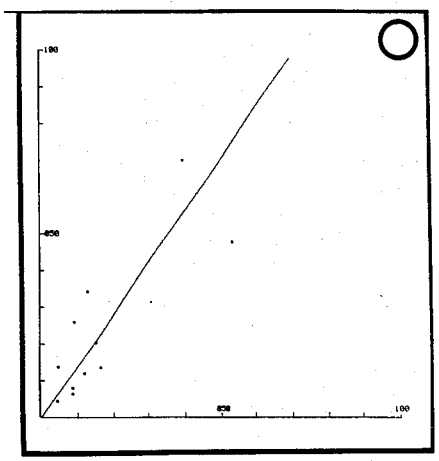

FIG. 3 shows the density versus density graphs for the $^{14}$C gel autoradiographs. The quenching effect is a general phenomenon, affecting all densities by the same ratio. For each graph, individual protein densits of the $^{14}$C unstained gels are plotted on the y-axis against the corresponding protein density in a stained gel.

EXAMPLE II

Mouse fibroblast cells are cultured and $^{14}$C incorporated by incubation of the cells in a $^{14}$C-amino acid mixture according to the process of Example I. At intervals of 0, 0.5, 1.0, 2.0 and 2.5 hours after labelling is begun, samples are taken and electrophoresced also according to the process of Example I. After electrophoresis, the gels are silver stained according to the process of Merril, U.S. Ser. No. 240,577 and each spot evaluated for total protein content by microdensitometric measurement. The gels are then dried, and the radioactivity of each spot is measured by scintillation counting (CPMs), according to Example I. The specific activity for a given protein "A" is obtained for each sample as CPM per unit (μg or mg) of protein ($C_{RP}/C_{TP}$). If the turnover is a first-order process, the first order rate constant "k" is calculated in the following manner from any two points:

| Time (hours after resuspension) | Specific Activity Of "A" in CPM/μg Protein |
|---|---|
| 0 | 9,987 CPM/μg |
| 0.5 | 13,181 |
| 1.0 | 22,962 |
| 2.0 | 30,306 |
| 2.5 | 40,000 |

$$k = \frac{2.3 \log \frac{1 \text{ hr specific activity}}{2.5 \text{ hr specific activity}}}{\Delta t} = \frac{2.3}{90} \log \frac{22,962}{40,000}, \text{ or } t_{\frac{1}{2}} = \frac{0.693}{k}$$

TABLE 1

CPM of solubilized proteins as percent of CPM of the

TABLE 1-continued corresponding unstained protein (after subtraction of background CPM), and percent density of protein spots on the autoradiograms and fluorograms as compared to the unstained gels.
(In some cases, quenching precluded protein density measurement of fluorograms.)

| Staining Method | $^3$H-labelled Proteins | | $^{14}$C-labelled Proteins | |
|---|---|---|---|---|
| | % CPM of Unstained Protein | % Density of Unstained Protein | % CPM of Unstained Protein | % Density of Unstained Protein |
| Unstained | 100% | 100% | 100% | 100% |
| Histological Silver Stain | 20 ± 2% | — | 54 ± 15% | 53 ∓ 3% |
| Photographic Silver Stain | 57 ± 7% | — | 78 ± 8% | 98 ∓ 6% |
| Histological Silver Stain (Silver Removed) | 13 ± 4% | — | 50 ± 16% | 48 ∓ 7% |
| Photographic Silver Stain (Silver Removed) | 32 ± 11% | 43 ∓ 9% | 47 ± 15% | 81 ∓ 10% |

What is claimed is:

1. In a method for determining polypeptide turnover rates of the type wherein radiolabelled proteins in a protein mixture extracted from a sample incubated with radioactive labelled amino acids are separated from the protein mixture, the improvement comprising employing $^{14}$C-labelled amino acids as the radioactive label for the synthesis of said proteins, silver staining the separated proteins and determining turnover rate by the amount of radioactive amino acid incorporated into protein per unit time/total protein.

2. The method of claim 1, wherein the proteins are separated by gel electrophoresis.

3. the method of claim 1, wherein the separated proteins are stained with a photographic silver stain.

4. The method of claim 1, wherein the separated proteins are stained with a histologic silver stain.

* * * * *